United States Patent
Dudney et al.

(10) Patent No.: US 7,465,288 B2
(45) Date of Patent: Dec. 16, 2008

(54) ACTUATION HANDLE FOR A CATHETER

(75) Inventors: Joshua L. Dudney, Minneapolis, MN (US); Donald George Goblish, Jr., Spring Park, MN (US); William Emerson Butler, Minneapolis, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 569 days.

(21) Appl. No.: 11/170,550

(22) Filed: Jun. 28, 2005

(65) Prior Publication Data

US 2007/0016164 A1  Jan. 18, 2007

(51) Int. Cl.
*A61M 31/00* (2006.01)
*A61M 25/00* (2006.01)

(52) U.S. Cl. ............................ 604/95.04; 604/523
(58) Field of Classification Search ............ 604/523, 604/95.04
See application file for complete search history.

(56) References Cited

U.S. PATENT DOCUMENTS

| | | | |
|---|---|---|---|
| 4,960,134 A | 10/1990 | Webster, Jr. | 128/786 |
| 5,125,895 A | 6/1992 | Buchbinder et al. | 604/95 |
| 5,125,896 A | 6/1992 | Hojeibane | 604/95 |
| 5,269,757 A | 12/1993 | Fagan et al. | 604/95 |
| RE34,502 E | 1/1994 | Webster, Jr. | 607/125 |
| 5,277,199 A | 1/1994 | DuBois et al. | 128/772 |
| 5,281,217 A | 1/1994 | Edwards et al. | 606/41 |
| 5,318,525 A | 6/1994 | West et al. | 604/95 |
| 5,327,889 A | 7/1994 | Imran | 128/642 |
| 5,327,905 A | 7/1994 | Avitall | 128/772 |
| 5,327,906 A | 7/1994 | Fideler et al. | |
| 5,330,466 A | 7/1994 | Imran | 606/13 |
| 5,342,295 A | 8/1994 | Imran | 604/43 |
| 5,354,297 A | 10/1994 | Avitall | 606/45 |
| 5,364,351 A | 11/1994 | Heinzelman et al. | |
| 5,383,923 A | 1/1995 | Webster, Jr. | 607/125 |
| 5,389,073 A | 2/1995 | Imran | 604/95 |
| 5,391,147 A | 2/1995 | Imran et al. | 604/95 |
| 5,395,328 A | 3/1995 | Ockuly et al. | 604/95 |
| 5,395,329 A | 3/1995 | Fleischhacker et al. | |
| 5,397,304 A | 3/1995 | Truckai | 604/95 |
| 5,431,168 A | 7/1995 | Webster, Jr. | 128/658 |
| 5,445,148 A | 8/1995 | Jaraczewski et al. | 128/642 |
| 5,478,330 A | 12/1995 | Imran et al. | 604/282 |
| 5,487,385 A | 1/1996 | Avitall | 128/642 |

(Continued)

FOREIGN PATENT DOCUMENTS

EP  1 205 208  5/2002

(Continued)

*Primary Examiner*—Nicholas D Lucchesi
*Assistant Examiner*—Victoria P Campbell

(57) ABSTRACT

A catheter actuation handle is disclosed for deflecting a distal end of a tubular catheter body including a first actuation wire extending from a proximal end of the body. The handle includes a grip portion for coupling to the proximal end of the body. A first actuator is moveably coupled to the grip portion. A first stationary gear rack is fixed relative to the grip portion. A first moveable gear rack is moveable relative to the grip portion and for coupling to the first actuation wire. A first pinion gear is coupled to the first actuator and located between, and engaged with, the first stationary gear rack and the first moveable gear rack.

30 Claims, 8 Drawing Sheets

U.S. PATENT DOCUMENTS

| | | | |
|---|---|---|---|
| 5,487,757 A | 1/1996 | Truckai et al. | 607/122 |
| 5,527,279 A | 6/1996 | Imran | 604/95 |
| 5,533,967 A | 7/1996 | Imran | 604/95 |
| 5,545,200 A | 8/1996 | West et al. | 607/122 |
| 5,562,619 A | 10/1996 | Mirarchi et al. | 604/95 |
| 5,582,609 A | 12/1996 | Swanson et al. | 606/39 |
| 5,588,964 A | 12/1996 | Imran et al. | 604/95 |
| 5,611,777 A | 3/1997 | Bowden et al. | 604/95 |
| 5,626,136 A | 5/1997 | Webster, Jr. | 128/642 |
| 5,656,029 A | 8/1997 | Imran et al. | 604/95 |
| 5,656,030 A | 8/1997 | Hunjan et al. | 604/95 |
| 5,755,760 A | 5/1998 | Maguire et al. | 607/122 |
| 5,779,669 A | 7/1998 | Haissaguerre et al. | 604/95 |
| 5,807,249 A | 9/1998 | Qin et al. | 600/374 |
| 5,826,576 A | 10/1998 | West | 128/642 |
| 5,827,272 A | 10/1998 | Breining et al. | 606/41 |
| 5,827,278 A | 10/1998 | Webster | 606/41 |
| 5,836,947 A | 11/1998 | Fleischman et al. | 606/47 |
| 5,842,984 A | 12/1998 | Avitall | 600/374 |
| 5,843,031 A | 12/1998 | Hermann et al. | 604/95 |
| 5,843,076 A | 12/1998 | Webster, Jr. et al. | 606/41 |
| 5,861,024 A | 1/1999 | Rashidi et al. | |
| 5,865,800 A | 2/1999 | Mirarchi et al. | 604/95 |
| 5,885,278 A | 3/1999 | Fleischman et al. | 606/41 |
| 5,897,529 A | 4/1999 | Ponzi | 604/95 |
| 5,910,129 A | 6/1999 | Koblish et al. | 604/95 |
| 5,916,213 A | 6/1999 | Haissaguerre et al. | 606/41 |
| 5,916,214 A | 6/1999 | Cosio et al. | 606/41 |
| 5,921,924 A | 7/1999 | Avitall | 600/374 |
| 5,931,811 A | 8/1999 | Haissaguerre et al. | 604/95 |
| 5,935,102 A | 8/1999 | Bowden et al. | 604/95 |
| 5,944,690 A | 8/1999 | Falwell et al. | 604/95 |
| 5,987,344 A | 11/1999 | West | 600/373 |
| 5,993,462 A | 11/1999 | Pomeranz et al. | 606/129 |
| 6,002,955 A | 12/1999 | Willems et al. | 600/374 |
| 6,024,722 A | 2/2000 | Rau et al. | |
| 6,027,473 A | 2/2000 | Ponzi | 604/95 |
| 6,033,403 A | 3/2000 | Tu et al. | 606/41 |
| 6,048,329 A | 4/2000 | Thompson et al. | 604/95 |
| 6,059,739 A | 5/2000 | Baumann | 600/585 |
| 6,064,902 A | 5/2000 | Haissaguerre et al. | 600/381 |
| 6,066,125 A | 5/2000 | Webster, Jr. | 604/528 |
| 6,068,629 A | 5/2000 | Haissaguerre et al. | 606/41 |
| 6,071,274 A | 6/2000 | Thompson et al. | 604/528 |
| 6,071,279 A | 6/2000 | Whayne et al. | 600/41 |
| 6,071,282 A | 6/2000 | Fleischman | 606/41 |
| 6,083,222 A | 7/2000 | Klein et al. | 606/41 |
| 6,090,104 A | 7/2000 | Webster, Jr. | 606/41 |
| 6,123,699 A | 9/2000 | Webster, Jr. | 604/528 |
| 6,138,043 A | 10/2000 | Avitall | 600/377 |
| 6,149,663 A | 11/2000 | Strandberg et al. | 606/180 |
| 6,156,034 A | 12/2000 | Cosio et al. | 606/41 |
| 6,169,916 B1 | 1/2001 | West | 600/373 |
| 6,171,277 B1 | 1/2001 | Ponzi | 604/95.04 |
| 6,178,354 B1 | 1/2001 | Gibson | 607/116 |
| 6,183,435 B1 | 2/2001 | Bumbalough et al. | 604/95.01 |
| 6,183,463 B1 | 2/2001 | Webster, Jr. | 604/528 |
| 6,198,974 B1 | 3/2001 | Webster, Jr. | 607/122 |
| 6,200,315 B1 | 3/2001 | Gaiser et al. | 606/41 |
| 6,203,507 B1 | 3/2001 | Wadsworth et al. | 600/585 |
| 6,203,525 B1 | 3/2001 | Whayne et al. | 604/528 |
| 6,210,362 B1 | 4/2001 | Ponzi | 604/95.01 |
| 6,210,407 B1 | 4/2001 | Webster | 606/41 |
| 6,214,002 B1 | 4/2001 | Fleischman et al. | 606/41 |
| 6,221,087 B1 | 4/2001 | Anderson et al. | 606/159 |
| 6,224,587 B1 | 5/2001 | Gibson | 604/528 |
| 6,241,754 B1 | 6/2001 | Swanson et al. | 607/99 |
| 6,308,091 B1 | 10/2001 | Avitall | 600/374 |
| 6,375,654 B1 | 4/2002 | McIntyre | 606/41 |
| 6,430,426 B2 | 8/2002 | Avitall | 600/374 |
| 6,454,758 B1 | 9/2002 | Thompson et al. | 604/528 |
| 6,582,536 B2 | 6/2003 | Shimada | |
| 2006/0142695 A1* | 6/2006 | Knudson | 604/95.04 |

FOREIGN PATENT DOCUMENTS

GB        1 170 018        11/1969

* cited by examiner

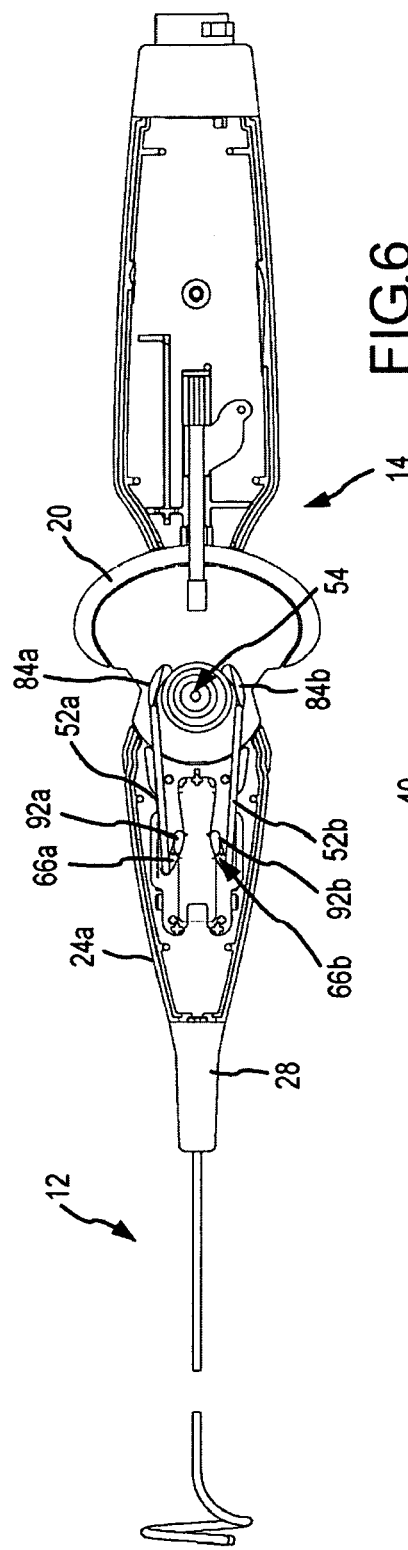
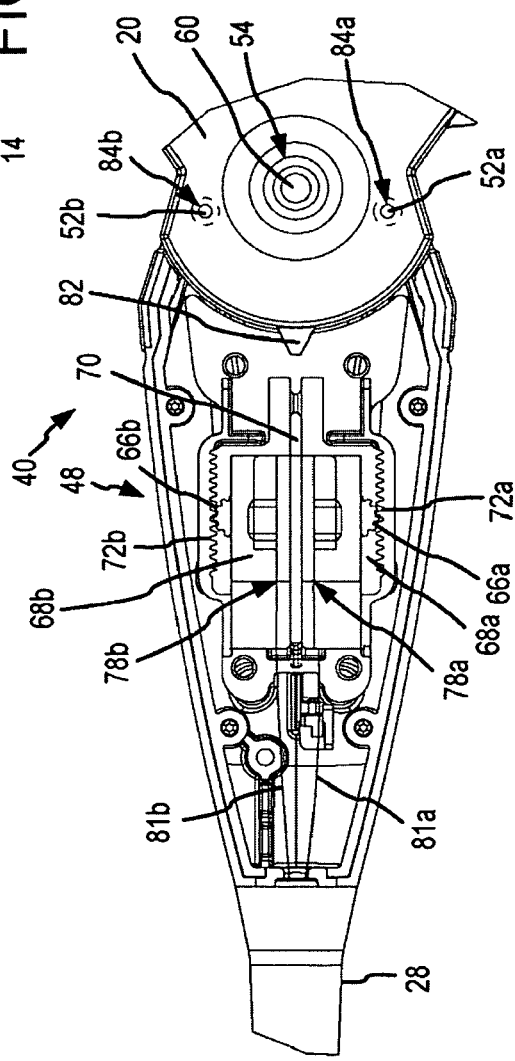
FIG. 6
FIG. 7

ACTUATION HANDLE FOR A CATHETER

FIELD OF THE INVENTION

The present invention relates to catheters and sheaths and methods of using catheters and sheaths. More particularly, the present invention relates to steerable catheter or sheath control handles and methods of manufacturing and using such handles.

BACKGROUND OF THE INVENTION

Catheters (or sheaths) with deflectable distal ends and actuation handles for controlling distal end deflection are used for many noninvasive medical procedures. For example, catheters having conductive electrodes along a distal end are commonly used for intra-cardiac electrophysiology studies. The distal portion of such a catheter is typically placed into the heart to monitor and/or record the intra-cardiac electrical signals during electrophysiology studies or during intra-cardiac mapping. The orientation or configuration of the catheter distal end is controlled via an actuator located on a handle outside of the body, and the electrodes conduct cardiac electrical signals to appropriate monitoring and recording devices that are operatively connected at the handle of the catheter.

Typically, these catheters include a generally cylindrical electrically non-conductive body. The main body includes a flexible tube constructed from polyurethane, nylon or other electrically non-conductive flexible material. The main body further includes braided steel wires or other non-metallic fibers in its wall as reinforcing elements. Each electrode has a relatively fine electrically conductive wire attached thereto and extending through the main body of the catheter. The conductive wire extends from the distal end to a proximal end where electrical connectors such as plugs or jacks are provided to be plugged into a corresponding socket provided in a recording or monitoring device.

The distal portion of the main body is selectively deformed into a variety of curved configurations using the actuator. The actuator is commonly internally linked to the distal portion of the catheter by at least one actuation wire. Some catheters employ a single actuation wire, which is pulled (i.e., placed in tension) by the actuator in order to cause the distal portion of the main body to deform. Other catheters have at least two actuation wires, where the actuation of one wire (i.e., placing one wire in tension) results in the other wire going slack (i.e., the wire does not carry a compressive load). In such catheters, where the actuation wires are not adapted to carry compressive loads (i.e., the actuation wires are only meant to be placed in tension), the actuation wires are commonly called pull or tension wires.

To deform the distal end of the catheter into a variety of configurations, a more recent catheter design employs a pair of actuation wires that are adapted such that one of the actuation wires carries a compressive force when the other actuation wire carries a tensile force. In such catheters, where the actuation wires are adapted to carry both compressive and tension loads, the actuation wires are commonly called push/pull or tension/compression wires and the corresponding catheter actuators are called push-pull actuators. U.S. Pat. No. 5,861,024 to Rashidi, which issued Jan. 19, 1999, is representative of a push-pull actuator of this type, and the details thereof are incorporated herein by reference.

While many of the existing catheter actuators provide precise operation and good flexibility in movement of the distal portion of the body, the existing actuators often offer a range of distal portion displacement that is less than desirable. In other words, the amount of push/pull of the actuation wires (i.e., the steering travel) is often inadequate for the medical procedure being performed. The inadequacy of the steering travel typically results from the generally limited size of the actuator body, which is usually sized for receipt and manipulation between the thumb and index finger of a user's hand. Accordingly, a need exists to provide an improved actuating assembly for a catheter that increases the amount of steering travel associated with the actuator.

SUMMARY OF THE INVENTION

The present invention, in one embodiment, is a catheter actuation handle for deflecting a distal end of a tubular catheter body including first, second and third actuation wires extending from a proximal end of the body. The handle comprises a grip portion, a first actuator, first and second stationary gear racks, first and second moveable gear racks, first and second pinion gears, and a second actuator. The grip portion is coupled to the proximal end of the body. The first actuator is moveably coupled to the grip portion. The first and second stationary gear racks are fixed relative to the grip portion. The first and second moveable gear racks are moveable relative to the grip portion and couple to the first and second actuation wires, respectively. The first pinion gear is coupled to the first actuator and located between, and engaged with, the first stationary gear rack and the first moveable gear rack. Similarly, the second pinion gear is coupled to the first actuator and located between, and engaged with, the second stationary gear rack and the second moveable gear rack. The second actuator is moveably coupled to the grip portion and adapted to displace the third actuation wire.

In one embodiment, the first actuator pivots laterally relative to a longitudinal axis of the grip portion. In one embodiment, the handle further comprises a first linkage and a second linkage. The first linkage extends between a first hole in the first actuator and a hole in the first pinion gear. The second linkage extends between a second hole in the first actuator and a hole in the second pinion gear. In one embodiment, the first and second holes in the first actuator are arcuate slots.

In one embodiment, the holes in the pinion gears are aligned with the axes of the pinion gears. In another embodiment, the holes in the pinion gears are offset from the axes of the pinion gears.

In one embodiment, when the actuator is in a neutral pivotal position, the first pinion gear is positioned at a distal end of the first stationary gear rack, and the second pinion gear is positioned at a distal end of the second stationary gear rack. Also, the first pinion gear is engaged with a proximal portion of the first moveable gear rack, and the second pinion gear is engaged with a proximal portion of the second gear rack.

In one embodiment, when the actuator is in a neutral pivotal position, the first pinion gear is positioned near a midpoint of the first stationary gear rack, and the second pinion gear is positioned near a midpoint of the second stationary gear rack. Additionally, the first pinion gear is engaged with a midpoint of the first moveable gear rack, and the second pinion gear is engage with a midpoint of the second moveable gear rack.

In one embodiment, a portion of the first actuator is displaceable through a portion of the second actuator. In one embodiment, the second actuator is longitudinally slideably displaceable relative to the grip portion.

In one embodiment, a lever is pivotally coupled to the grip portion and coupled at a first end to the second actuator and at a second end to the third actuation wire. Specifically, a cable is coupled to the second actuator and extends around an arcuate side of the lever beginning at the first end of the lever, and a linkage couples the third actuation wire to the second end of the lever.

In one embodiment, the linkage includes a slide block slideably received in the grip portion and coupled to the third actuation wire. In one embodiment, the linkage further includes a link extending between the slide block and the second end. In one embodiment, the link is a clevis.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 6 is a bottom plan view of the handle with the lower grip portion removed to reveal portions of the first and second actuation mechanisms.

FIG. 7 is the same view depicted in FIG. 4, except of a second embodiment of the first actuator.

DETAILED DESCRIPTION OF THE INVENTION

Figure 1:
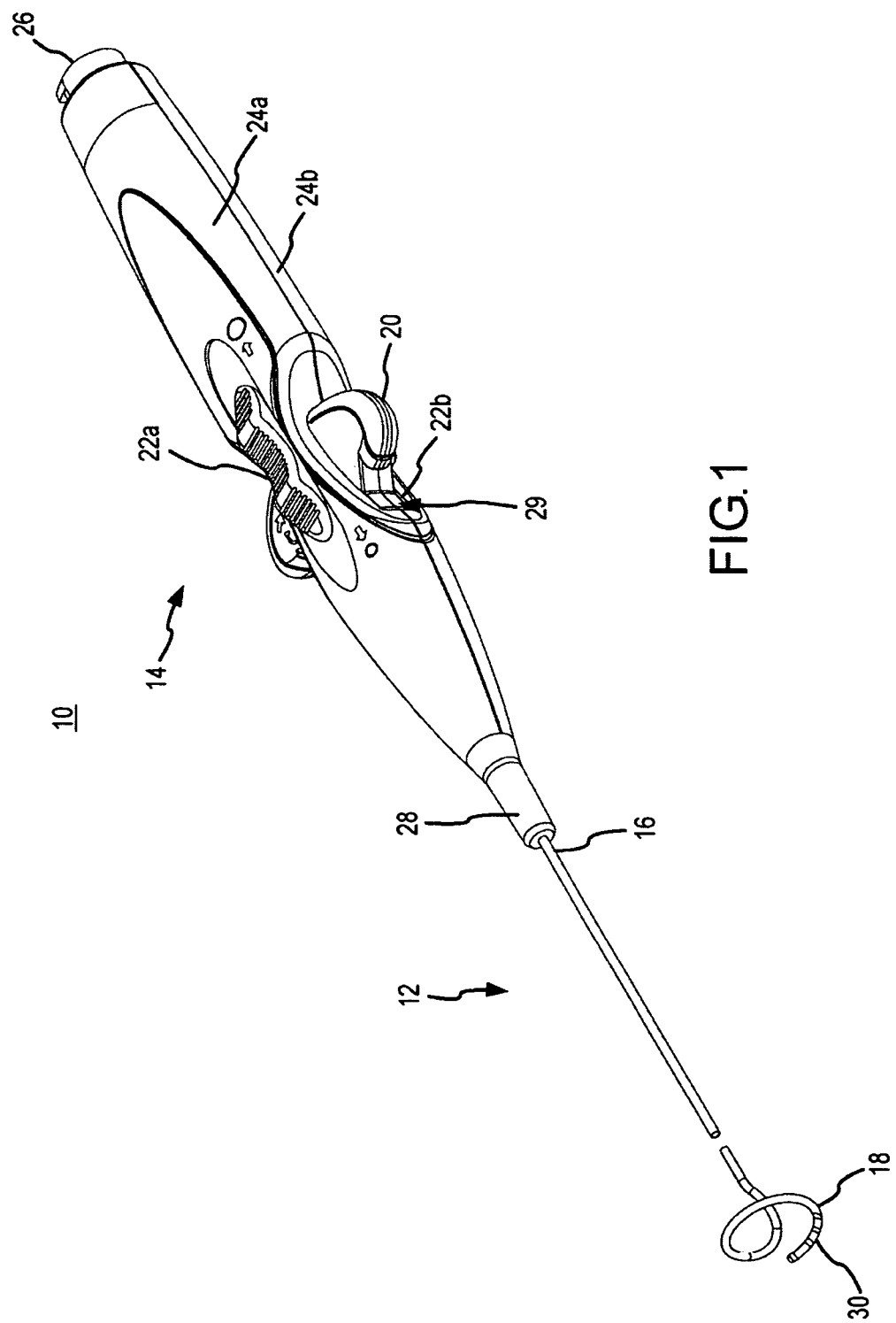
FIG. 1 is an isometric view of the catheter (or sheath) of the present invention.

FIG. 1 is an isometric view of the catheter (or sheath) 10 of the present invention. As shown in FIG. 1, in one embodiment, the catheter 10, which is an electrophysiology, RF ablation, or similar catheter (or sheath) 10, includes an elongated flexible generally cylindrical hollow body 12 and an ergonomically shaped actuation handle 14 coupled to a proximal end 16 of the body 12. The actuation handle 14 is adapted to control the deflection of a deflectable distal end 18 of the body 12.

As will be understood from the following discussion, the catheter 10 is advantageous for several reasons. First, the actuation handle 14 has a novel rack and pinion actuation mechanism that provides significantly increased steering travel of the distal end 18 of the body 12, as compared to prior art actuation handles. Second, in one embodiment, the actuation mechanism is configured such that it does not compress the actuation wires. Third, in one embodiment, the actuation mechanism is configured such that the actuation force perceived by a user is minimized and generally constant over the full range of displacement, as compared to prior art actuation mechanisms. Fourth, in one embodiment where the body 12 includes three actuation wires extending through the body 12 from the distal end 18 to the actuation handle 14, the handle has a second actuation mechanism that is configured to actuate the third actuation wire.

As shown in FIG. 1, in one embodiment, the actuation handle 14 includes a first actuator 20, upper and lower buttons 22a, 22b of a second actuator, upper and lower grip portions 24a, 24b, an electrical plug 26 at the proximal end of the handle 14, and a strain relief 28 at the distal end of the handle 14. The upper and lower grip portions 24a, 24b define a space 29 that extends laterally through the grip portions 24a, 24b. The first actuator 20 is pivotally coupled to the grip portions 24a, 24b and resides in the space 29. The first actuator 20 may pivotally displace laterally relative to the grip portions 24a, 24b through the space 29. Such pivotal displacement of the first actuator 20 allows a user to bi-directionally deflect the distal end 18 of the body 12.

In one embodiment, the upper and lower buttons 22a, 22b of the second actuator are slideably coupled to their respective grip portions 24a, 24b in such a manner that they may slideably displace along their respective grip portions 24a, 24b in a direction that is generally parallel to the longitudinal axis of the handle 14. Such slideable displacement of the buttons 22a, 22b of the second actuator allows a user to deflect the distal end 18 of the body 12 in a third direction. For example, as indicated in FIG. 1, in one embodiment where the distal end 18 forms a loop or lariat, the first actuator 20 causes the distal end 18 to deflect bi-directionally right or left, and the buttons 22a, 22b of the second actuator cause the distal end 18 to increase or decrease the diameter of its loop or lariat. In another embodiment, as taught in U.S. patent application Ser. No. 10/784,511 to Rashidi, which was filed on Feb. 23, 2004 (issued as U.S. Pat. No. 7,245,955 on Jul. 17, 2007) and is hereby incorporated by reference in its entirety into this application, the first actuator 20 causes the distal end 18 to bi-directionally loop and to increase or decrease the extent to which the distal end 18 loops. The buttons 22a, 22b of the second actuator cause the loop or lariat formed by the distal end 18 to nod or deflect.

As illustrated in FIG. 1, the distal end 18 of the body 12 includes plural spaced electrodes 30. Each electrode 30 is connected to a fine electrical conductor wire that extends to the electrical plug 26 through the body 12, the strain relief 28, and the handle 14. The electrical plug 26 is adapted to be connected to a recording, monitoring, or RF ablation device. In one embodiment, the body 12 is typically polyurethane, nylon or any suitable electrically non-conductive material. The body 12 serves as at least a portion of the blood-contacting segment of the catheter 10 and is vascularly inserted into a patient by methods and means well known in the art.

In one embodiment, first and second actuation wires extend from the distal end 18, through the body 12, and into the handle 14 to couple to the actuation mechanism of the first actuator 20 as will be discussed in detail below. In one embodiment, an additional third actuation wire extends from the distal end 18, through the body 12, and into the handle 14 to couple to the actuation mechanism of the second actuator.

In one embodiment, the actuation wires are pull or tension wires (i.e., the actuation wires are not adapted to support a compressive load). In another embodiment, the actuation wires and the body 12 are configured such that the actuation wires are pull/push or tension/compression wires (i.e., the actuation wires are adapted to support a compressive load). Thus, in the context of the first and second actuation wires, when one actuation wire is placed in tension, the other actuation wire will carry a compressive load. In one embodiment, the actuation wires are formed from a super elastic Nitinol wire or another suitable material. Detailed discussion regarding the configuration of the body 12 and its three actuation wires is provided in the aforementioned incorporated U.S. patent application.

Figure 2:
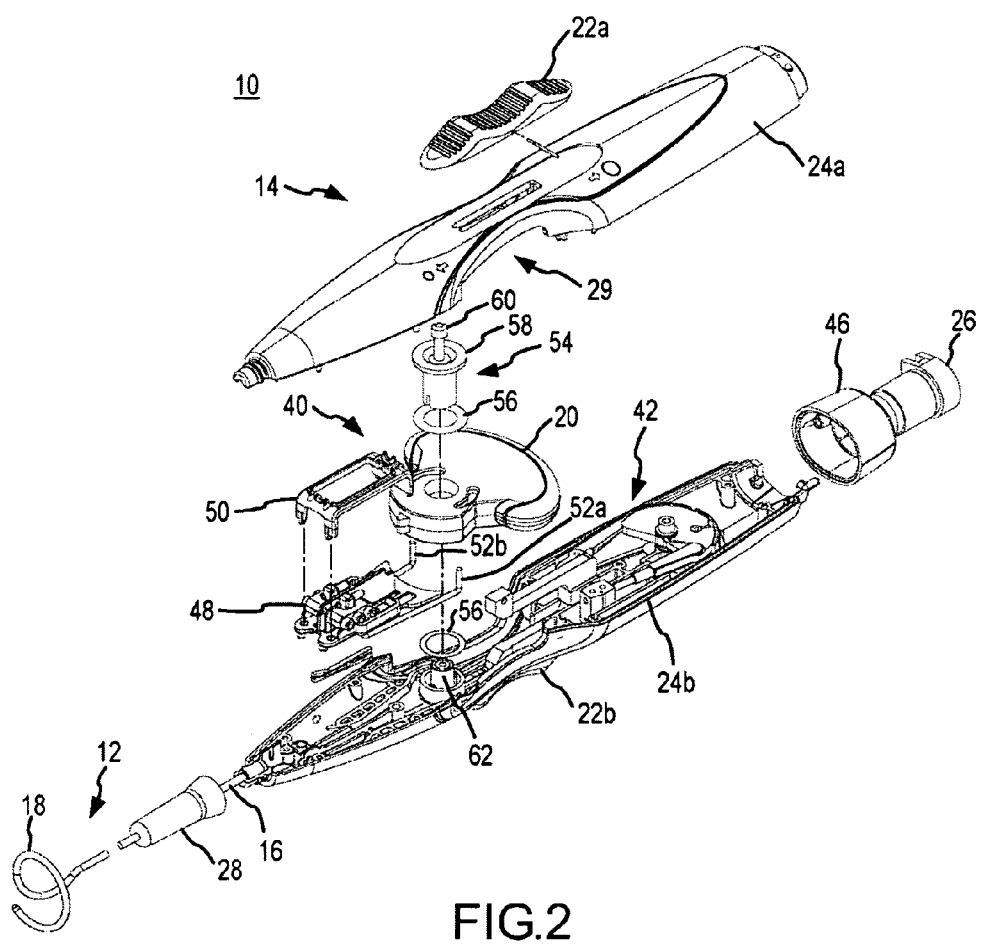
FIG. 2 is an isometric view of the handle with the upper and lower grip portions separated and the first actuation mechanism exploded to better illustrate its various components.

For a detailed discussion of one embodiment of the handle 14 of the subject invention, reference is now made to FIG. 2, which is an isometric view of the handle 14 with the upper and lower grip portions 24a, 24b separated and the first actuation mechanism 40 exploded to better illustrate its various components. As shown in FIG. 2, the grip portions 24a, 24b of the handle 14 are adapted to matingly couple with each other and serve as an enclosure and mounting base for the first and second actuation mechanisms 40, 42. The first actuation mechanism 40 is mounted in a distal portion of the handle 14, and the second actuation mechanism 42 is mounted in a proximal portion of the handle 14. The electrical plug 26 is mounted in a proximal end assembly 46 that serves as the proximal end of the handle 14.

As illustrated in FIG. 2, the first actuation mechanism 40 includes the first actuator 20, a gear assembly 48 with a cover 50, first and second control arms 52a, 52b and a pivot assembly 54. The pivot assembly 54 pivotally couples the first actuator 20 to the lower grip portion 24b and includes washers 56, a bushing 58 and a hex-head screw 60 for attaching the pivot assembly 54 as an integral unit to a pivot base 62 on the lower grip portion 24b. As shown in FIG. 2, each washer 56 is a different size.

Figure 3:
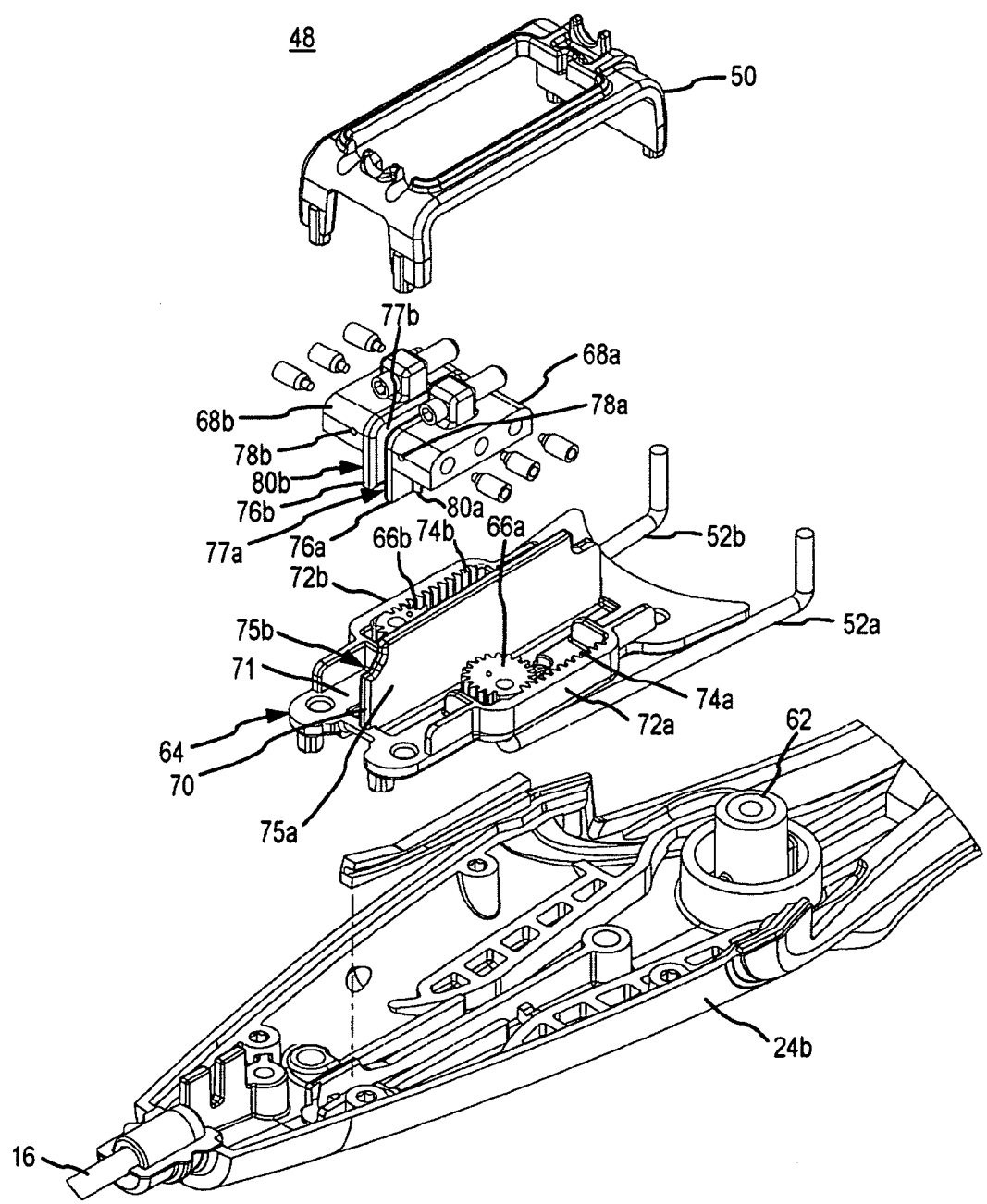
FIG. 3 is an exploded isometric view of the gear assembly.

For a detailed discussion of the gear assembly 48, reference is now made to FIG. 3, which is an exploded isometric view of the gear assembly 48. As shown in FIG. 3, the gear assembly 48 includes a frame 64, first and second pinion gears 66a, 66b, first and second wire blocks 68a, 68b, and the cover 50. The frame 64 includes a face plate 70, a base or floor 71, and first and second stationary gear racks 72a, 72b. The first and second stationary gear racks 72a, 72b are fixed to the lateral sides of the base 71 of the frame 64 and oriented such that their respective teeth sides 74a, 74b face each other and are generally parallel to the longitudinal centerline of the frame 64. The face plate 70 is aligned with the longitudinal centerline of the frame 64, positioned between the two stationary gear racks 72a, 72b, and generally perpendicular to the base 71 of the frame 64. Each vertical side or face 75a, 75b of the faceplate 70 is generally planar.

As indicated in FIG. 3, each wire block 68a, 68b includes a movable gear rack 76a, 76b, a generally planar vertically oriented face 77a, 77b, and a hole 78a, 78b. Each movable gear rack 76a, 76b extends downwardly from its respective wire block 68a, 68b and has teeth 80a, 80b on one side and a generally planar vertical face 77a, 77b on the other. The moveable gear racks 76a, 76b are oriented such that they are generally parallel to each other, their teeth 80a, 80b face away from each other, and their planar faces 77a, 77b face each other in a generally parallel arrangement.

Each hole 78a, 78b is adapted to receive a proximal end of one of the first and second actuation wires. For example, as illustrated in FIG. 4, which is a top plan view of a first embodiment of the first actuation mechanism 40 mounted in the proximal portion of the lower grip portion 24b, the first and second actuation wires 81a, 81b are received in their respective holes 78a, 78b upon exiting the proximal end 16 of the body 12.

Figure 4:
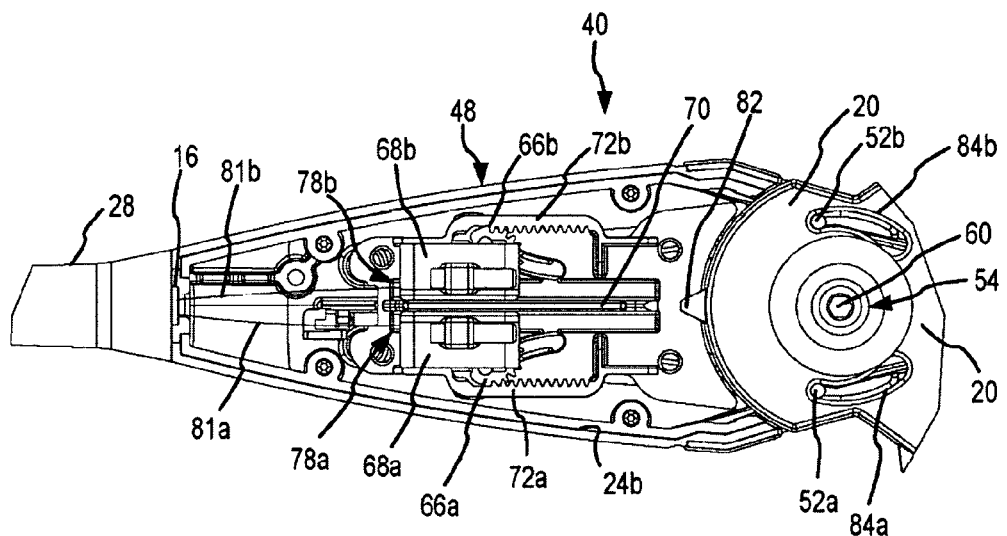
FIG. 4 is a top plan view of a first embodiment of the first actuation mechanism mounted in the proximal portion of the lower grip portion, wherein the first and second actuation wires are received in their respective holes in the wire blocks.

As shown in FIG. 4, the actuator 20 is pivotally mounted to the lower grip portion 24b via the pivot assembly 54. The first actuation assembly 40 is located distal to the actuator 20 and proximal to the to the strain relief 28. In one embodiment, the first actuator 20 includes a position indicator point 82 on its most distal edge and first and second openings 84a, 84b that are located on opposite lateral sides of the actuator 20.

As indicated in FIG. 4, a proximal end of a control arm 52a, 52b resides in each opening 84a, 84b. In a first embodiment of the first actuation mechanism 48, as depicted in FIG. 4, the openings 84a, 84b are arcuate slots 84a, 84b that are substantially longer in length than the diameter of the control arm 52a, 52b.

Figure 5:
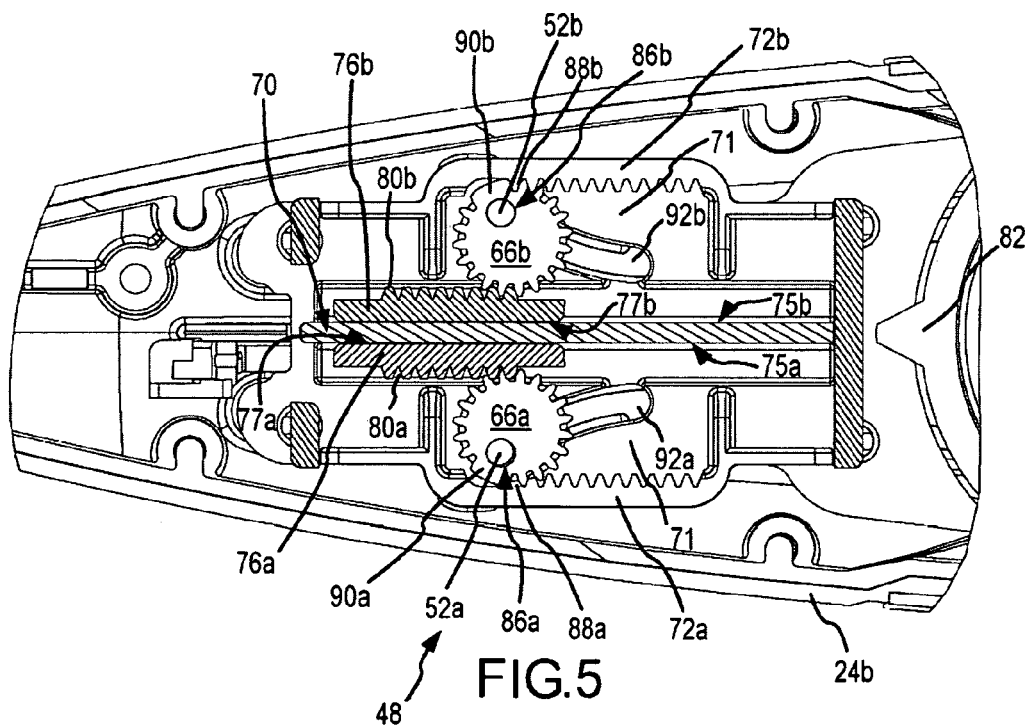
FIG. 5 is an enlarged plan view of the gear assembly with the top portions of the wire blocks removed to better illustrate the gearing arrangement.

As illustrated in FIG. 5, which is an enlarged plan view of the gear assembly 48 with the top portions of the wire blocks 68a, 68b removed to better illustrate the gearing arrangement, a distal end of a control arm 52a, 52b resides in a hole 86a, 86b in each pinion gear 66a, 66b. In one embodiment, each hole 86a, 86b is positioned at the axial center of its respective pinion gear 66a, 66b. In another embodiment, as depicted in FIG. 5, each hole 86a, 86b is offset from the axial center of its respective pinion gear 66a, 66b.

As shown in FIG. 6, which is a bottom plan view of the handle 14 with the lower grip portion 24b removed to reveal portions of the first and second actuation mechanisms 40, 42, each control arm 52a, 52b extends between its respective points of connection with a hole 86a, 86b of a pinion 66a, 66b and an opening 84a, 84b in the first actuator 20. Thus, as can be understood from FIGS. 4-6, the control arms 52a, 52b serve as linkages to transmit the motion of the first actuator 20 to the pinions 66a, 66b.

As illustrated in FIG. 5, each pinion gear 66a, 66b is positioned between, and engaged with, a stationary gear rack 72a, 72b and a moveable gear rack 76a, 76b. A generally planar back 77a, 77b of each moveable gear rack 76a, 76b slideably abuts against a respective generally planar face 75a, 75b of the faceplate 70.

As shown in FIG. 5, in one embodiment, where the hole 86a, 86b in each pinion 66a, 66b is offset from the pinion's axial center, when the pinion 66a, 66b is positioned at the most distal end of the stationary gear rack 72, 72b, the hole 86a, 86b will be located immediately adjacent, and slightly distal to, the most distal tooth 88a, 88b of the respective stationary gear rack 72a, 72b. In one embodiment, to prevent the pinions 66a, 66b from over traveling relative to the gear racks 72a, 72b, 76a, 76b, a blank toothless section 90a, 90b exists along the circumference of each pinion 66a, 66b next to the pinion's hole 86a, 86b.

As shown in FIGS. 5 and 6, an arcuate slot 92a, 92b exists between each pair of gear racks 72a, 72b, 76a, 76b in a base or floor portion 71 of the frame 64. Each arcuate slot 92a, 92b serves as a pathway through which the distal portion of each control arm 52a, 52b may pass as the respective pinion gear 66a, 66b displaces along the stationary gear rack 72a, 72b. The arcuate configuration of the arcuate slots 92a, 92b allows the distal parts of each control arm 52a, 52b to follow the sinusoidal displacement of the holes 86a, 86b when the pinions 66a, 66b displace along the stationary gear racks 72a, 72b.

Because the holes 86a, 86b are offset from the axial centers of the pinions 66a, 66b, a mechanical advantage is created as compared to a configuration where the holes 86a, 86b are centered at the axial centers of the pinions 66a, 66b. The mechanical advantage results in an actuation force, as perceived by a user, that is less than and more constant than the actuation forces required to operate prior art catheters.

The operation of the first embodiment of the first actuation mechanism 40, wherein the each opening 84a, 84b is an arcuate slot 84a, 84b, will now be described while referencing FIGS. 4-6. As indicated in FIGS. 4-6, when the first actuation mechanism 40 is in a neutral pivotal position (i.e., when the wire blocks 68a, 68b are both in their most proximal positions and the position indicator point 82 is facing distally and is generally aligned with the longitudinal centerline of the lower grip portion 24b, as depicted in FIG. 4), the proximal end of each control arm 52a, 52b is in the most distal portion of its respective arcuate slot 84a, 84b. This configuration of the first embodiment of the first actuation mechanism 40 is advantageous where the actuation wires 81a, 81b are tension or pull type actuation wires. More specifically, it is advantageous where the actuation wires 81a, 81b are only to be placed in tension and never to be compressed, thereby avoiding buckling of the actuation wires 81a, 81b.

For example, as can be understood from FIGS. 4-6, when the first actuator 20 is pivoted in a first direction (e.g., counterclockwise in FIG. 4), the proximal end of the first control arm 52a is engaged by the distal end of the first arcuate slot 84a and the first control arm 52a is pulled proximally. This causes the distal end of the first control arm 52a to cause the first pinion gear 66a to displace proximally along the corresponding stationary gear rack 72a. The rotation of the first pinion gear 66a causes the corresponding moveable gear rack 76a to be driven proximally. As can be understood from FIG. 4, this causes the corresponding wire block 68a to place the first actuation wire 81a in tension as the wire block 68a proximally displaces.

While pivoting the actuator 20 in the first direction causes the first wire block 68a to act on the first actuation wire 81a, such a movement, generally speaking, has no impact on the second wire block 68b or the second actuation wire 81b. This is because a counter clockwise rotation of the actuator 20 simply causes the second arcuate slot 84b to slide along the proximal end of the control arm 52b without the proximal end of the second arcuate slot 84b encountering the proximal end of the control arm 52b. As a result, the first actuator 20 does not distally drive the second control arm 52b and the second wire block 68b is not caused to distally displace. Accordingly, the second actuation wire 81b is not placed in tension or compression when the actuator 20 is pivoted in the first direction (i.e., counterclockwise). In other words, the second actuation wire 81b is allowed to relax and move freely.

In one embodiment, when the actuator 20 is pivoted back to the neutral pivotal position depicted in FIG. 4, the proximal end of the first arcuate slot 84a does not encounter the proximal end of the first control arm 52a. As a result, the first actuator 20 does not drive the first wire block 68a and its corresponding actuation wire 52a distally back into the neutral position. Instead, the tension that the deflected distal end 18 exerts on the first actuation wire 52a causes the wire 52a and its corresponding block 52a to return to the neutral position.

Continuing the example, as can be understood from FIGS. 4-6, when the first actuator 20 is pivoted in a second direction (i.e., clockwise in FIG. 4), the proximal end of the second control arm 52b is engaged by the distal end of the second arcuate slot 84b and the second control arm 52b is pulled proximally. This causes the distal end of the second control arm 52b to cause the second pinion gear 66b to displace proximally along the corresponding stationary gear rack 72b. The rotation of the second pinion gear 66b causes the corresponding moveable gear rack 76b to be driven proximally. As can be understood from FIG. 4, this causes the corresponding wire block 68b to place the second actuation wire 81b in tension as the wire block 68b proximally displaces.

While pivoting the actuator 20 in the second direction causes the second wire block 68b to act on the second actuation wire 81b, such a movement, generally speaking, has no impact on the first wire block 68a or the first actuation wire 81a. This is because a clockwise rotation of the actuator 20 simply causes the first arcuate slot 84a to slide along the proximal end of the control arm 52a without the proximal end of the first arcuate slot 84a encountering the proximal end of the control arm 52a. As a result, the first actuator 20 does not distally drive the first control arm 52a and the first wire block 68a is not caused to distally displace. Accordingly, the first actuation wire 81a is not placed in tension or compression when the actuator 20 is pivoted in the second direction (i.e., clockwise). In other words, the first actuation wire 81a is allowed to relax and move freely.

In one embodiment, when the actuator 20 is pivoted back to the neutral pivotal position depicted in FIG. 4, the proximal end of the second arcuate slot 84b does not encounter the proximal end of the second control arm 52b. As a result, the first actuator 20 does not drive the second wire block 68b and its corresponding actuation wire 52b distally back into the neutral position. Instead, the tension that the deflected distal end 18 exerts on the second actuation wire 52b causes the wire 52b and its corresponding block 52b to return to the neutral position.

As can be understood from FIGS. 4 and 5, because of the gearing arrangement, the proximal linear displacement of a moveable gear rack 76a, 76b and, as a result, its corresponding actuation wire 81a, 81b is generally twice the proximal linear displacement of the corresponding pinion gear 66a, 66b. This is because the proximal displacement of a moveable gear rack 76, 76b is the sum of a pinion gear's linear proximal displacement along a stationary gear rack 72a, 72b plus the pinion gear's rotational displacement.

Figure 8:
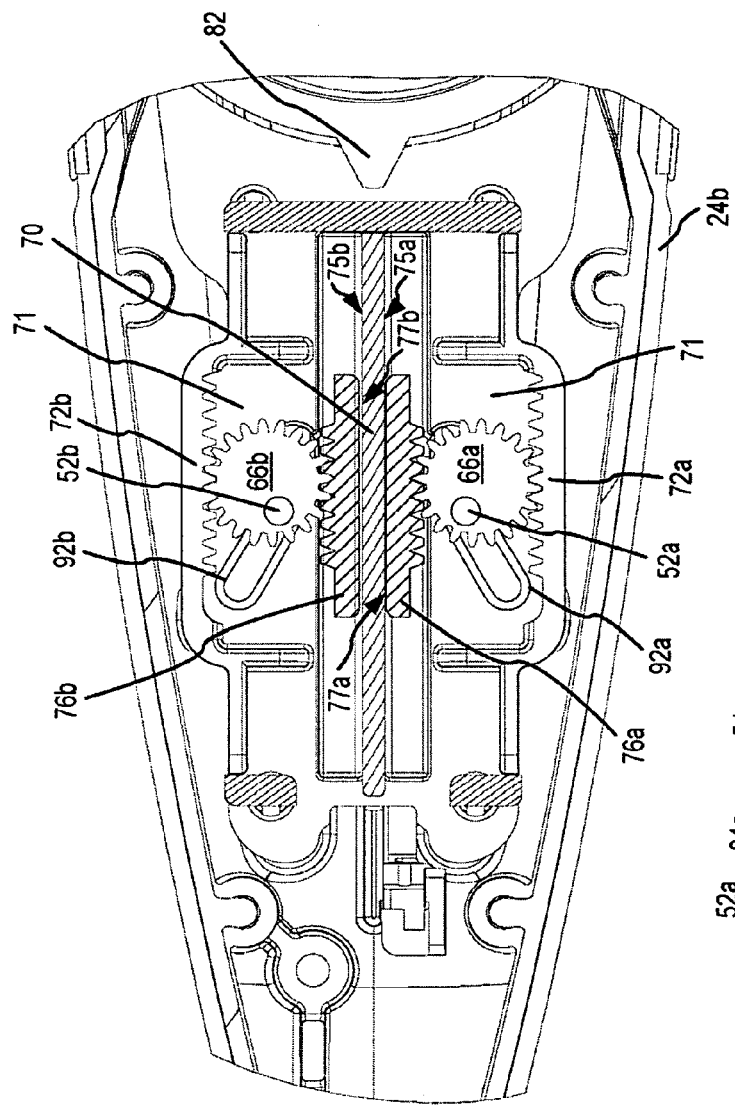
FIG. 8 is the same view depicted in FIG. 5, except of the second embodiment of the first actuator.
Figure 9:
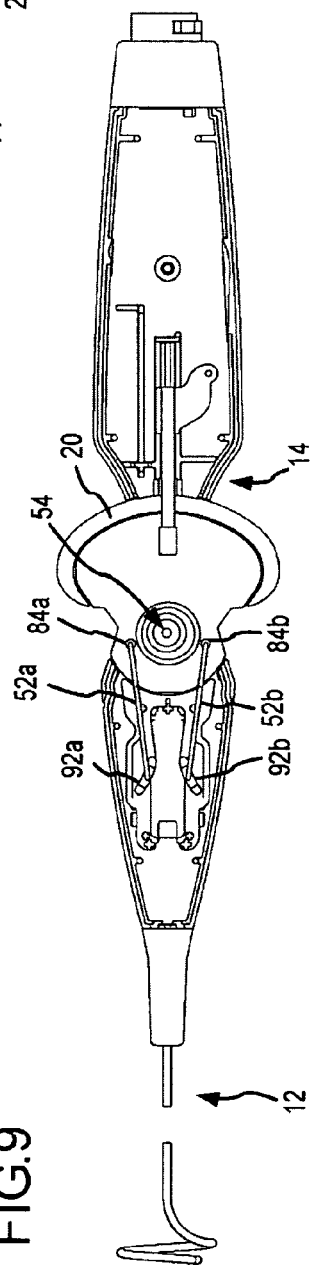
FIG. 9 is the same view depicted in FIG. 6, except of the second embodiment of the first actuator.

For a discussion of a second embodiment of the first actuation mechanism 40, reference is now made to FIGS. 7-9. FIGS. 7-9 are, respectively, the same views depicted in FIGS. 4-6, except of the second embodiment of the first actuation mechanism 40. Generally speaking, the features of the first and second embodiments of the first actuation mechanism 40 are the same, except as provided in the following discussion.

As shown in FIG. 7, unlike the arcuate slots 84a, 84b of the first embodiment of the actuation mechanism 40 (as discussed in reference to FIGS. 4-6), the openings 84a, 84b of the second embodiment are circular holes 84a, 84b with diameters generally equal to the diameter of the control arms 52a, 52b. As indicated in FIG. 7, a proximal end of a control arm 52a, 52b resides in each circular opening 84a, 84b.

As can be understood from FIGS. 7-9, in the second embodiment of the actuation mechanism 40, when the first actuation mechanism 40 is in a neutral pivotal position (i.e., the position indicator point 82 is facing distally and generally aligned with the longitudinal centerline of the lower grip portion 24b, as depicted in FIG. 7), each pinion 66a, 66b is positioned approximately midway along both of the lengths of its respective stationary gear rack 72a, 72b and moveable gear rack 76a, 76b. This arrangement allows the control arms 52a, 52b to oppositely and equally move relative to each other when the actuator 20 is pivoted. This movement is brought about in the second embodiment of the first actuation mechanism 40 because, unlike the arcuate slots 84a, 84b of the first embodiment, the circular openings 84a, 84b of the second embodiment prevent displacement between the proximal ends of the control arms 52a, 52b and the actuator 20. The configuration of the second embodiment of the first actuation mechanism 40 is advantageous where the actuation wires 81a, 81b are pull/push or tension/compression type actuation wires.

For example, as can be understood from FIGS. 7-9, when the first actuator 20 is pivoted in a first direction (e.g., counterclockwise in FIG. 7), the proximal end of the first control arm 52a is pulled proximally by the first circular opening 84a, and the proximal end of the second control arm 52b is pushed distally by the second circular opening 84b. Accordingly, the distal end of the first control arm 52a pulls the first pinion gear 66a proximally along its corresponding stationary gear rack 72a, and the distal end of the second control arm 52b pushes the second pinion gear 66b distally along its corresponding stationary gear rack 72b. The rotation of the first pinion gear 66a proximally drives its corresponding moveable gear rack 76a, and the rotation of the second pinion gear 66b distally drives its corresponding moveable gear rack 76b. As can be understood from FIG. 7, this causes the first wire block 68a to place the first actuation wire 81a in tension as the wire block 68a proximally displaces. Also, this causes the second wire block 68b to push (i.e., compress) the second actuation wire 81b distally as the second wire block 68b distally displaces.

As can be understood from FIGS. 7-9, pivoting the first actuator 20 in a second direction (i.e., clockwise) reverses the movement of the control arms 52a, 52b. Accordingly, the second wire block 68b moves proximally (i.e., the second actuation wire 81b is placed into tension), and first wire block 68a moves distally (i.e., the first actuation wire 81a is compressed).

Figure 10:
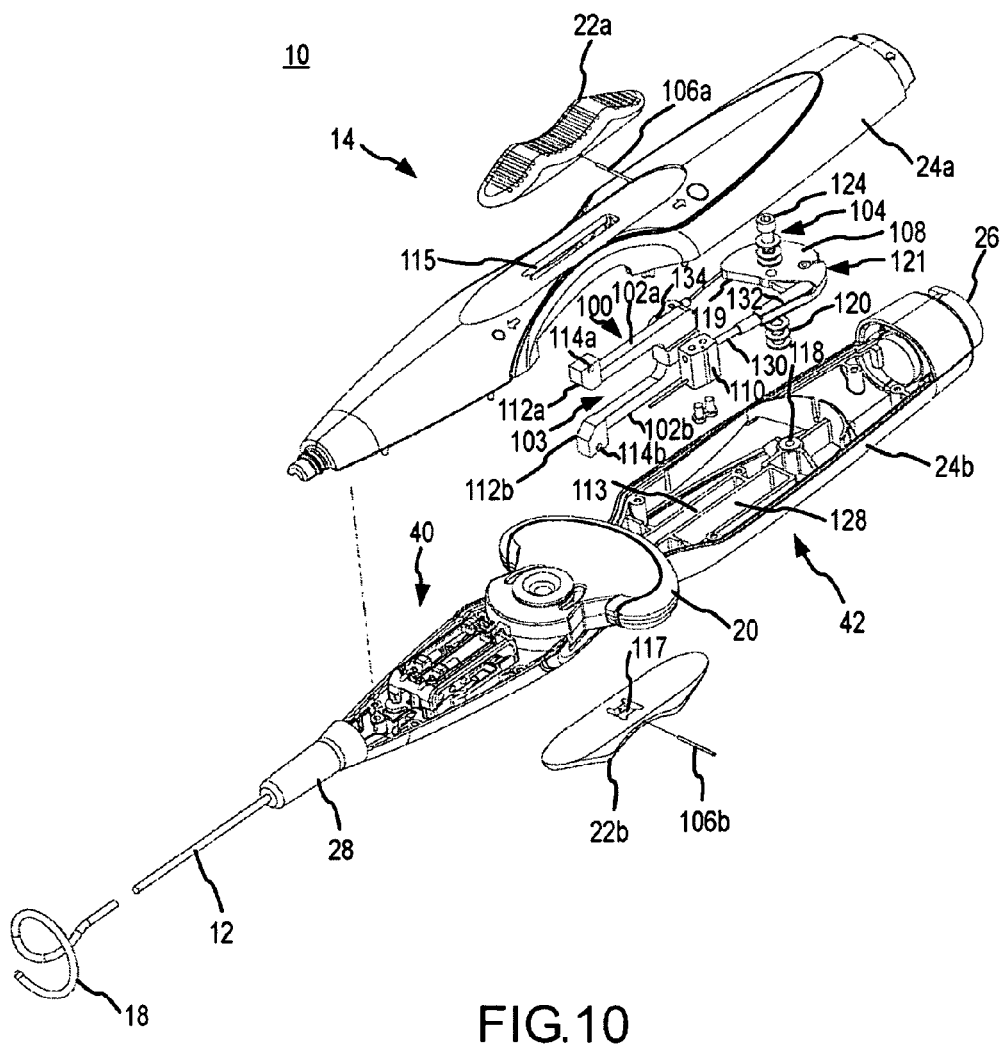
FIG. 10 is an isometric view of the handle with the upper and lower grip portions separated and the second actuation mechanism exploded to better illustrate its various components.

For a detailed discussion of one embodiment of the second actuation mechanism 42, reference is now made to FIG. 10, which is an isometric view of the handle 14 with the upper and lower grip portions 24a, 24b separated and the second actuation mechanism 42 exploded to better illustrate its various components. As shown in FIG. 10, the second actuation mechanism 42 is mounted in a proximal portion of the handle 14 and includes a second actuator 100 with upper and lower arms 102a, 102b, the upper and lower buttons 22a, 22b of the second actuator 100, a pivot assembly 104, upper and lower pins 106a, 106b, a lever 108, and a slide block 110.

As illustrated in FIG. 10, in one embodiment, the second actuator 100 is generally U-shaped. The second actuator's arms 102a, 102b are generally vertically aligned and offset from each other in a parallel arrangement to form a gap 103 through which the proximal portion of the first actuator 20 displaces. The lower arm 102b slideably resides in a longitudinal slot or groove 113 in the lower grip portion 22b. Similarly, the upper arm 102a slideably resides in a longitudinal slot or groove in the upper grip portion 22a.

As shown in FIG. 10, each arm 102a, 102b includes a head 112a, 112b with a pinhole 114a, 114b for receiving a pin 106a, 106b. The upper head 112a extends through a longitudinal slot 115 in the upper grip portion 24a to couple to the upper button 22a. Similarly, the lower head 112b extends through a longitudinal slot in the lower grip portion 24b to couple to the lower button 22b. The lower head 112b resides in a seat 117 in the lower button 22b and is coupled thereto via the pin 106b. Likewise, the upper head 112a resides in a seat in the upper button 22a and is coupled thereto via the pin 106a. Because each button 22a, 22b is coupled to an arm 102a, 102b of the second actuator 100, the buttons 22a, 22b are slaved together.

As indicated in FIG. 10, the heads 112a, 112b are slideably displaceable within their respective longitudinal slots 115. Thus, when a user slides the buttons 22a, 22b longitudinally relative to the grip portions 24a, 24b to actuate the second actuation assembly 42, the arms 102a, 102b and heads 112a, 112b slideably displace in their respective slots 113, 115.

As shown in FIG. 10, the lever 108 is pivotally coupled to a pivot base 118 in the lower grip portion 24b via the pivot assembly 104. The pivot assembly 104 includes a series of washers 120 (including a Belleville spring washer to compensate for compression set or material creep during the catheter's shelf life), and a hex-head screw 124 for securing the pivot assembly 104 to the pivot base 118 as one integral unit. When the hex-head screw 124 is properly tightened, the pivot assembly 104 is configured such that it provides a tension drag feature that holds the lever 108 in place although the user has released the buttons 22a, 22b. As a result, the user does not need to maintain contact with the buttons 22a, 22b to maintain the distal end 18 in a set position once placed there by the user actuating the second actuation mechanism 42.

As illustrated in FIG. 10, in one embodiment, the lever 108 is generally semicircular such that it has a generally linear edge 119 and a generally arcuate edge 121 extending between the first and second ends of the linear edge 119. The linear edge 119 is adjacent the pivot assembly 104 and faces generally distally. In one embodiment, the radius of the arcuate edge 121 is generally equal to the distance between the arcuate edge 121 and the axis of the pivot assembly 104. The arcuate edge 121 faces generally proximally.

Figure 11:
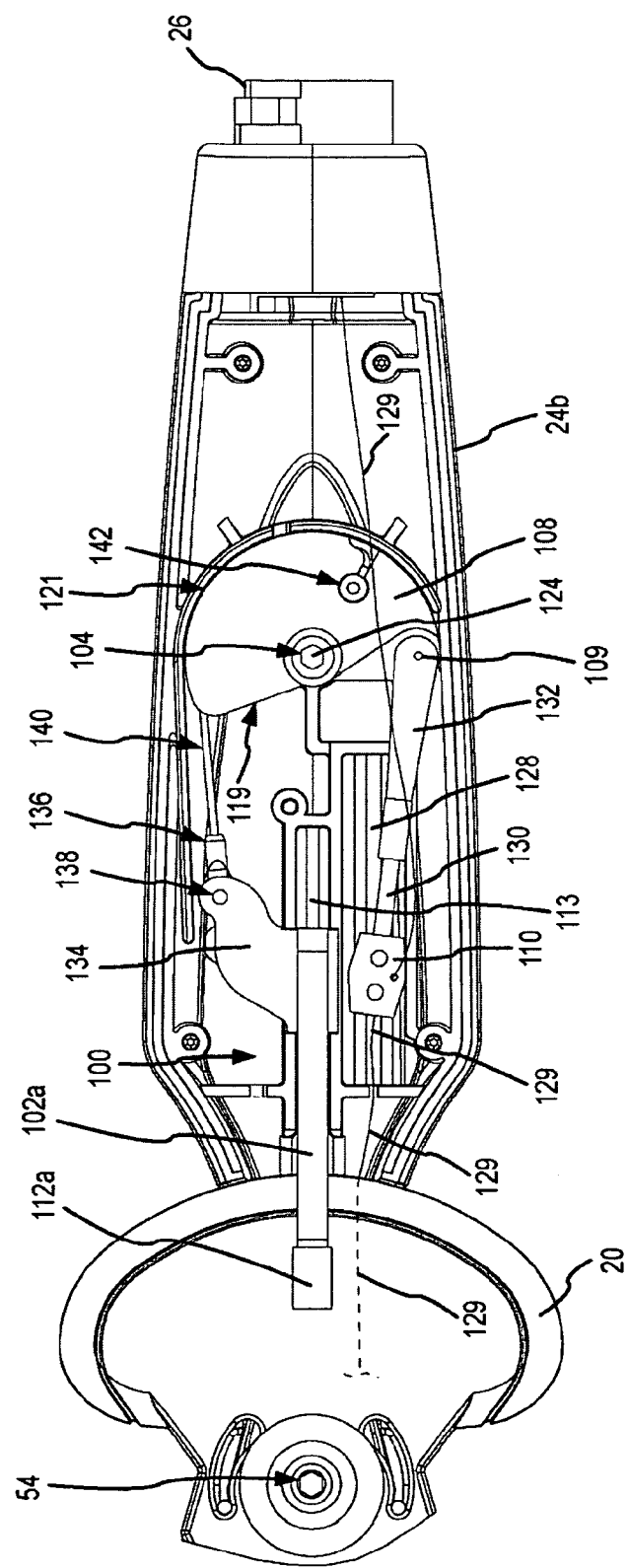
FIG. 11 is a top plan view of the second actuation mechanism mounted in the lower grip portion with the upper grip portion removed.

For further discussion of the components of the second actuation mechanism 42, reference is now made to FIG. 11, which is a top plan view of the second actuation mechanism 42 mounted in the lower grip portion 24b with the upper grip portion 24a removed. As indicated in FIG. 11, a bottom end of the slide block 110 is slideably received in a lower groove or slot 128 in the lower grip portion 24b. Similarly, a top end of the slide block 110 is slideably received in an upper groove or slot in the upper grip portion 24a. The slots 128 are generally parallel to the longitudinal axis of the handle 14.

As illustrated in FIG. 11, a third actuation wire 129 extends from the distal end 18 of the body 12 and into the handle 14 to couple the slide block 110. In one embodiment, the third actuation wire 129 also serves as an electrical wire leading from one or more electrodes 30 in the distal tip 18 to the electrical plug 26 in the proximal end of the handle 14. In doing so, the third actuation wire 129 passes through, and couples to, the slide block 110.

As shown in FIG. 11, a threaded rod 130 extends between a proximal side of the slide block 110 and a clevis 132 pivotally attached to a first end of the lever 108 via a pin 109. The threads on the threaded rod 130 allow the distance between the clevis 132 and the slide block 110 to be adjusted. Thus, the initial actuation wire position relative to the lever 108 can be adjusted via the threaded rod 130.

As indicated in FIG. 11, an arm 134 extends from the proximal end of the second actuator 100 in a direction opposite from the slide block 110. A link 136 is pivotally coupled to an end of the arm 134 via a pin 138. A cable 140 is coupled to the link 136 and extends to and around the arcuate side 121 of the lever 108 to couple to the lever 108 via an attachment feature 142 (e.g., a screw, bolt, pin, etc.). The arcuate side 121 of the lever 108 is grooved or slotted to receive the cable 140. The cable 140 and arcuate side 121 of the lever 108 operate together like a belt and pulley such that a moment arm between the cable 140 and the pivotable lever 108 remains constant as the lever 108 pivots.

As can be understood from FIG. 11, when actuating the third actuation wire 129 to cause the distal end 18 of the body 12 to deflect, a user displaces a button 22a, 22b distally, which causes the U-shaped second actuator 100 to displace distally. As a result, the arm 134 pulls the cable 140 distally, thereby causing the lever 108 to pivot in a counterclockwise direction about the pivot assembly 104. This pivoting movement causes the clevis 132 to pull the slide block 110 in a proximal direction. The proximal movement of the slide block 110 places the third actuation wire 129 into tension (i.e., it pulls the third actuation wire 129), which causes the distal end 18 of the body 12 to deflect.

Increasingly deflecting the distal end of the body 12 requires an increasing force. Thus, during the initial stages of distal end deflection of the body 12, the force needed to pull the third actuation wire 129 is lower than at the final stages of distal end deflection. The increasing force needed to further increase the deflection of the distal end of the body 12 is addressed by the configuration between the clevis 132 and the lever 108. Specifically, the configuration between the clevis 132 and the lever 108 is such that the moment arm changes as the lever 108 pivots.

The moment arm length between the clevis 132 and the pivot assembly 104 of the lever 108 is greatest during the initial stages of distal tip deflection (i.e., when the pin 109 is at its most distal position). Because of the configuration between the clevis 132 and the lever 108, the length of the moment arm decreases as the distal end 18 is increasingly deflected (i.e., the pin 109 moves proximally). Consequently, the mechanical advantage at the buttons 22a, 22b is the least when the actuation wire tension is low (i.e., during the initial stages of distal end deflection) and the most when the actuation wire tension is high (i.e., during the last stages of distal end deflection approaching full deflection).

As can be understood from FIG. 11, to allow the deflected distal end 18 to return to its non-deflected configuration, a user proximally displaces a button 22a, 22b, which causes the U-shaped second actuator 100 to proximally displace. This provides slack in the cable 140, which allows the lever 108 to pivot clockwise as the spring force stored in the deflected distal end 18 acts to distally pull the third actuation wire 129 and, as a result, the slide block 110 as the distal end 18 springs back into a non-deflected configuration.

In use, the body 12 of the catheter 10 is inserted into the patient in a manner well known in the art. An operator grasps the handle 14 and manipulates the first actuator 20 between his thumb and finger. Advantageously, the first actuator 20 protrudes from each side of the handle 14 to allow for such ease of movement and manipulation. The first actuator 20 is moved relative to the handle 14, which causes the first and second actuation wires 78a, 78b to be displaced via the first actuation mechanism 40. As a result, the distal end 18 of the body 12 deflects.

To deflect the distal end 18 of the body 12 in another manner, the user distally slides the buttons 22a, 22b with a thumb or finger. This causes the third action wire 129 to displace via the second actuation mechanism 42. As a result, the distal end 18 of the body 12 deflects in manner different from the deflection brought about by the actuation of the first actuation mechanism 40.

Although the present invention has been described with reference to preferred embodiments, persons skilled in the art will recognize that changes may be made in form and detail without departing from the spirit and scope of the invention. The invention is limited only by the scope of the following claims.

What is claimed is:

1. A catheter actuation handle for deflecting a distal end of a tubular catheter body including a first actuation wire extending from a proximal end of the body, the handle comprising: a grip portion for coupling to the proximal end of the body; a first actuator moveably coupled to the grip portion; a first stationary gear rack including gear teeth, the first stationary gear rack fixed relative to the grip portion; a first moveable gear rack moveable relative to the grip portion and for coupling to the first actuation wire; and a first pinion gear coupled to the first actuator and located between, and engaged with, the first stationary gear rack and the first moveable gear rack.

2. The handle of claim 1, wherein the first actuator is pivotal relative to the grip portion.

3. The handle of claim 2, wherein the first actuator pivots laterally relative to a longitudinal axis of the grip portion.

4. The handle of claim 1, further comprising a linkage extending between a hole in the first actuator and a hole in the first pinion gear.

5. The handle of claim 4, wherein the hole in the first actuator is an arcuate slot.

6. The handle of claim 4, wherein the hole in the first pinion gear is aligned with an axial center of the first pinion gear.

7. The handle of claim 4, wherein the hole in the first pinion gear is offset from an axial center of the first pinion gear.

8. The handle of claim 1, further comprising a second actuator moveably coupled to the grip portion and adapted to displace a second actuation wire extending from the proximal end of the body.

9. The handle of claim 8, wherein a portion of the first actuator is displaceable through a portion of the second actuator.

10. The handle of claim 8, wherein the second actuator is longitudinally slideably displaceable relative to the grip portion.

11. The handle of claim 8, further comprising a lever pivotally coupled to the grip portion and coupled at a first end to the second actuator and at second end to the second actuation wire.

12. The handle of claim 11, further comprising a cable coupled to the second actuator and extending around an arcuate side of the lever beginning at the first end of the lever.

13. The handle of claim 12, further comprising a linkage coupling the second actuation wire to the second end of the lever.

14. The handle of claim 13, wherein the linkage includes a slide block slideably received in the grip portion and coupled to the second actuation wire.

15. The handle of claim 14, wherein the linkage further includes a link extending between the slide block and the second end.

16. The handle of claim 15, wherein the link includes a clevis.

17. The handle of claim 1, further comprising: a second stationary gear rack fixed relative to the grip portion; a second moveable gear rack moveable relative to the grip portion and for coupling to a second actuation wire extending from the proximal end of the body; and a second pinion gear coupled to the first actuator and located between, and engaged with, the second stationary gear rack and the second moveable gear rack.

18. The handle of claim 17, wherein the first actuator is pivotal relative to the grip portion.

19. The handle of claim 18, further comprising a first linkage and a second linkage, wherein the first linkage extends between a first hole in the first actuator and a hole in the first pinion gear, and wherein the second linkage extends between a second hole in the first actuator and a hole in the second pinion gear.

20. The handle of claim 19, wherein the first and second holes in the first actuator are arcuate slots.

21. The handle of claim 19, wherein when the actuator is in a neutral pivotal position, the first pinion gear is positioned at a distal end of the first stationary gear rack, and the second pinion gear is positioned at a distal end of the second stationary gear rack.

22. The handle of claim 21, wherein when the actuator is in said neutral pivotal position, the first pinion gear is engaged with a proximal portion of the first moveable gear rack, and the second pinion gear is engaged with a proximal portion of the second gear rack.

23. The handle of claim 19, wherein when the actuator is in a neutral pivotal position, the first pinion gear is positioned near a midpoint of the first stationary gear rack, and the second pinion gear is positioned near a midpoint of the second stationary gear rack.

24. The handle of claim 23, wherein when the actuator is in said neutral pivotal position, the first pinion gear is engaged with a midpoint of the first moveable gear rack, and the second pinion gear is engage with a midpoint of the second moveable gear rack.

25. The handle of claim 17, further comprising a second actuator moveably coupled to the grip portion and adapted to displace a third actuation wire extending from the proximal end of the body.

26. The handle of claim 25, wherein a portion of the first actuator is displaceable through a portion of the second actuator.

27. The handle of claim 25, wherein the second actuator is longitudinally slideably displaceable relative to the grip portion.

28. The handle of claim 25, further comprising a lever pivotally coupled to the grip portion and coupled at a first end to the second actuator and at second end to the third actuation wire.

29. The handle of claim 28, further comprising a cable coupled to the second actuator and extending around an arcuate side of the lever beginning at the first end of the lever.

30. The handle of claim 29, further comprising a linkage coupling the third actuation wire to the second end of the lever.

* * * * *